(12) United States Patent
Kump et al.

(10) Patent No.: US 6,460,003 B1
(45) Date of Patent: Oct. 1, 2002

(54) APPARATUS AND METHOD FOR RESOLUTION CALIBRATION OF RADIOGRAPHIC IMAGES

(75) Inventors: Kenneth Scott Kump, Waukesha, WI (US); Jeffrey A. Kautzer, Waukesha, WI (US); Richard Aufrichtig, Mountain View, CA (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/346,517

(22) Filed: Jul. 1, 1999

(51) Int. Cl.[7] .............................................. G01D 18/00

(52) U.S. Cl. ........................................ 702/85; 382/128

(58) Field of Search .............................. 702/69, 85, 88, 702/90, 109; 382/128, 132, 274, 299; 250/370.09, 370.11

(56) References Cited

U.S. PATENT DOCUMENTS

| | | | |
|---|---|---|---|
| 4,315,318 A | 2/1982 | Kato et al. | 382/264 |
| 4,674,125 A | 6/1987 | Carlson et al. | 382/303 |
| 4,716,414 A | 12/1987 | Luttrell et al. | 382/240 |
| 4,718,104 A | 1/1988 | Anderson | 32/179 |
| 4,731,865 A * | 3/1988 | Seivenpiper | 382/54 |
| 4,868,651 A | 9/1989 | Chou et al. | 378/98.7 |
| 4,891,757 A | 1/1990 | Shroy, Jr. et al. | 378/98.7 |

(List continued on next page.)

FOREIGN PATENT DOCUMENTS

| | | |
|---|---|---|
| EP | 0 776 149 A1 | 5/1997 |
| EP | 0 901 104 A2 | 3/1999 |
| GB | 2 046 052 A | 11/1980 |

OTHER PUBLICATIONS

Digital Image Processing, pp. 263–302, William K. Pratt, 1991.
Multiresolution Image Processing and Analysis, pp. 10–15, A. Rosenfield, Ed., 1984.
Contrast Enhancement Using Burt Pyramid Processing, pp. 352–353, Society for Information Display, 1986.
Leszczynski, et al. "Digital Contrast Enhancement for Online Portal Imaging" *Medical & biological Engineering & Computing*, 27(5):507–512 (Sep. 1, 1989).

*Primary Examiner*—Patrick Assouad
*Assistant Examiner*—Manuel L. Barbee
(74) *Attorney, Agent, or Firm*—McAndrews, Held & Malloy, Ltd.; Peter J. Vogel; Michael A. Dellapenna (57) ABSTRACT

A method and apparatus for calibrating the resolution of a medical imaging system measures unadjusted performance of a digital image detector used in the medical imaging system. The method then determines a weighting coefficient for a spatial frequency band processed by the medical imaging system. The weighting coefficient is based on a desired performance of the digital image detector and the unadjusted performance of the digital image detector. The method stores the weighting coefficient for subsequent application to the spatial frequency band by the medical imaging system. Identical or distinct weighting coefficients may be used at multiple spatial resolution levels. A single weighting coefficient may applied to all pixels at a given spatial resolution, or numerous spatial resolution variation compensation coefficients may be used in different regions of each spatial resolution. A resolution calibration subsystem for a medical imaging system employing a digital image detector includes a memory storing digital image data. A processor, through dedicated hardware, or a hardware/software combination determines a spatial frequency band of the image data and applies a weighting coefficient to the first spatial frequency band. The weighting coefficient is based on a desired resolution (for example, expressed as a desired Modulation Transfer Function) of the digital image detector and a measured resolution (for example, a measured Modulation Transfer Function) of the digital image detector.

23 Claims, 4 Drawing Sheets

U.S. PATENT DOCUMENTS

| | | | |
|---|---|---|---|
| 4,920,428 A | 4/1990 | Lin et al. | 358/461 |
| 4,969,204 A | 11/1990 | Melnychuck et al. | 382/240 |
| 5,075,883 A * | 12/1991 | Friedman et al. | 702/109 |
| 5,224,177 A | 6/1993 | Doi et al. | 382/168 |
| 5,461,655 A | 10/1995 | Vuylsteke et al. | 382/274 |
| 5,467,404 A | 11/1995 | Vuylsteke et al. | 378/62 |
| 5,506,880 A | 4/1996 | Scardino et al. | 378/98.2 |
| 5,528,659 A * | 6/1996 | Heidsieck | 378/56 |
| 5,546,473 A | 8/1996 | Buytaert et al. | 382/132 |
| 5,644,662 A | 7/1997 | Vuylsteke et al. | 382/302 |
| 5,693,948 A | 12/1997 | Sayed et al. | 250/370.09 |
| 5,760,403 A * | 6/1998 | Elabd | 250/370.11 |
| 6,266,625 B1 * | 6/2001 | Johnson | 702/89 |

* cited by examiner

APPARATUS AND METHOD FOR RESOLUTION CALIBRATION OF RADIOGRAPHIC IMAGES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention generally relates to medical diagnostic imaging systems, and in particular relates to resolution calibration in medical imaging systems employing digital detectors.

X-ray imaging has long been an accepted medical diagnostic tool. X-ray imaging systems are commonly used to capture, as examples, thoracic, cervical, spinal, cranial, and abdominal images that often include the information necessary for a doctor to make an accurate diagnosis. When having a thoracic X-ray image taken, for example, a patient stands with his or her chest against an X-ray sensor as an X-ray technologist positions the X-ray sensor and an X-ray source at an appropriate height. The X-ray sensor then detects the X-ray energy generated by the source and attenuated to various degrees by different parts of the body. An associated control system (where the X-ray sensor is a solid digital image detector) scans out the detected X-ray energy and prepares a corresponding diagnostic image on a display. If the X-ray sensor is conventional film, the film is subsequently developed and displayed using a backlight.

In any imaging system, X-ray or otherwise, image quality is of primary importance. In this regard, X-ray imaging systems that use digital image detectors ("digital X-ray systems"), face certain unique difficulties. In particular, digital X-ray systems must meet stringent demands on Critical to Quality (CTQ) measurements including image resolution (both in an absolute sense, and in uniformity across an image), image resolution consistency (e.g., from system to system and over time), and image noise. In the past, however, digital X-ray systems were often unable to meet CTQ parameters or provide consistent image quality across detectors, in part due to process variations in the semiconductor fabrication techniques used to manufacture solid state digital image detectors, or inherently due to the imaging technology.

Thus, for example, two different digital X-ray systems at a single location may have a noticeable variation in perceived image quality, even though both systems pass the CTQ measurements. Doctors or technicians may then unnecessarily consider one machine inferior to another, refrain from using one or more capable machines, or spend time trying to resolve image differences between the two digital X-ray systems. Furthermore, the digital X-ray system provider may incur the time and expense of responding to maintenance calls to address the perceived digital X-ray system variation, only to find that both digital X-ray systems are within specification (or to incur great expense of time and money to find a digital image detector for the perceived inferior machine that matches the perceived superior system).

As noted above, the characteristics of digital image detectors inherently vary. Although there is a need to provide consistent image quality (and in particular, image resolution) across multiple digital imaging systems, there has been in the past no automated technique for providing such consistency. Furthermore, the stringent CTQ measures may result in low acceptable yields for digital image detectors which are then destroyed, or, at best, unusable for medical diagnostic systems. Consequently, time, money, and resources are wasted.

A need has long existed in the industry for a method and apparatus for providing control over resolution in digital imaging systems that overcome the problems noted above, and others previously experienced.

SUMMARY OF THE INVENTION

A preferred embodiment of the present invention provides a method and apparatus for calibrating resolution of a digital imaging system. The method and apparatus include measuring unadjusted performance of a first digital image detector used in the imaging system. The method and apparatus then determine a weighting coefficient for a first spatial frequency band processed by the medical imaging system. Each spatial frequency bands processed may, for example, be formed using a multiresolution decomposition technique, such as a Burt pyramid decomposition. The weighting coefficient is based on a predetermined desired performance of the digital image detector and the measured performance of the digital image detector. The weighting coefficient may also be based on a target performance or target resolution. The weighting coefficient is stored for subsequent application to the spatial frequency band by the medical imaging system. Identical or distinct weighting coefficients may be used at multiple spatial resolution levels. A single weighting coefficient may be applied to all pixels at a given spatial resolution, or numerous spatial resolution variation compensation coefficients may be used in different regions of each spatial frequency band. The calibration may be generalized to continuous time systems using a calibration factor rather than discrete weighting coefficients.

The preferred embodiment also provides a resolution calibration subsystem for a digital imaging system employing a digital image detector. The resolution calibration subsystem includes a memory storing digital image data (e.g., image data acquired from a digital image detector such as a solid state X-ray detector) and a processor coupled to the memory. The processor, through dedicated hardware, or a hardware/software combination determines a first spatial frequency band of the image data and applies a weighting coefficient to the first spatial frequency band. The weighting coefficient is based on a predefined desired resolution (for example, expressed in terms of a predefined desired Modulation Transfer Function) of the digital image detector and a measured resolution (for example, in terms of a measured Modulation Transfer Function) of the digital image detector. Again, the calibration may be generalized to continuous time systems using a filter with frequency response characterized by the calibration factor.

DETAILED DESCRIPTION OF THE PREFERRED EMBODIMENT

Figure 1:
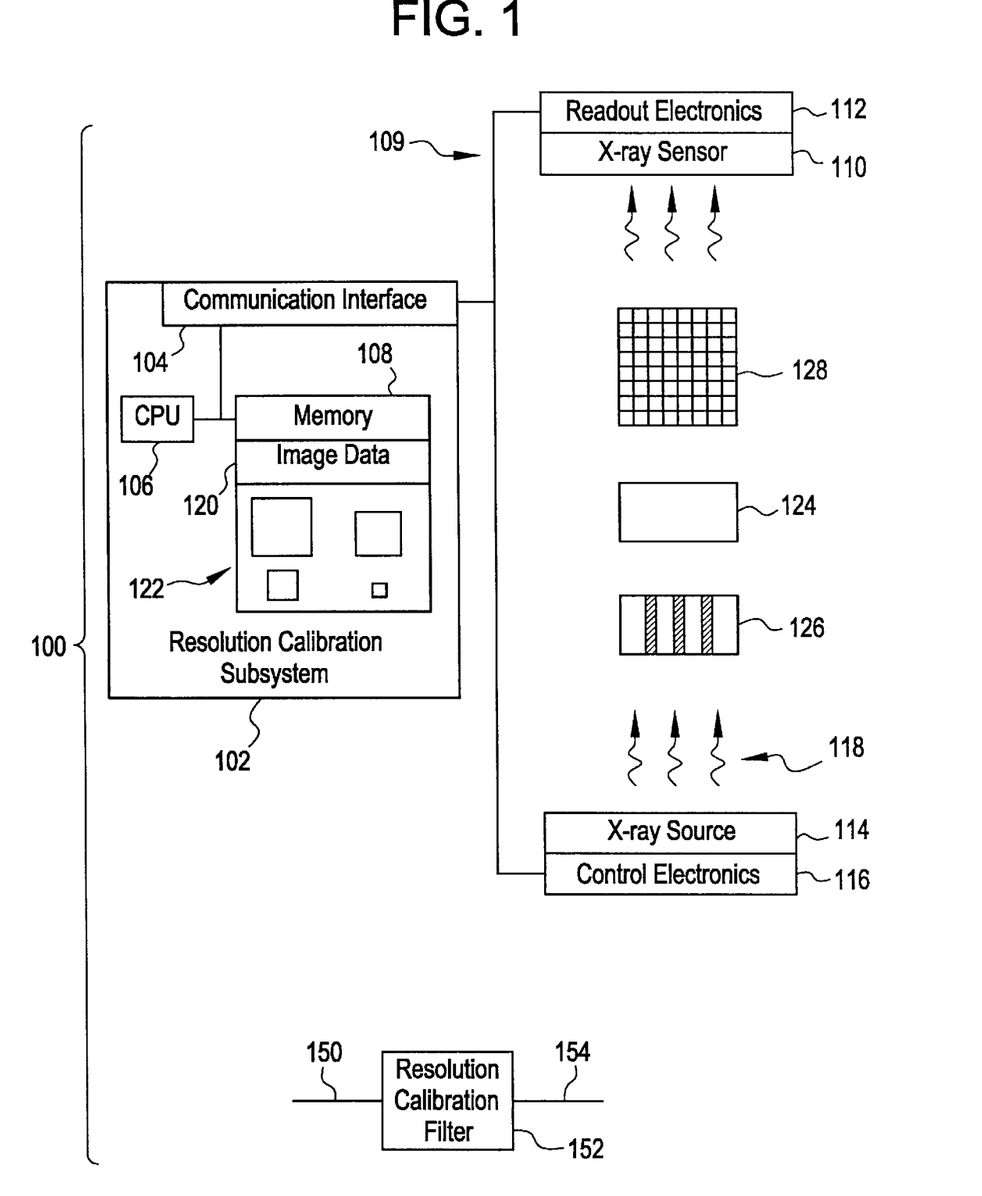
FIG. 1 presents a medical imaging system incorporating a resolution calibration subsystem.

Turning to FIG. 1, that figure shows a medical imaging system 100 incorporating a resolution calibration subsystem 102. The resolution subsystem 102 includes a communication interface 104, a CPU 106, and a program/data memory system 108. Connected to the communication interface 104 is a digital image detector 109 shown in FIG. 1 as an X-ray sensor 110 (with associated readout electronics 112). An energy source is shown in FIG. 1 as an X-ray source 114 having associated control electronics 116. The X-ray source 114 generates X-ray energy 118 that the X-ray sensor 110 detects.

Stored in the memory 108 is image data 120 (e.g., pixel values representative of an image level) acquired from the digital image detector 109. The memory 108 further stores a multiresolution decomposition 122 of the image data 120. Also illustrated in FIG. 1 are a flat phantom 124, a bar pattern phantom 126, and a uniformity mesh 128.

The X-ray sensor 110 is preferably a solid state X-ray detector. The X-ray source 114 and control electronics 116 may be found in commercially available X-ray tube assemblies.

The resolution calibration subsystem 102 uses the communications interface 104 to acquire digital image data 120 from the digital image detector 109. The communications interface 104 may be any general purpose communications interface, including a serial, parallel, industrial, or network interface. The CPU 106 may be, for example, a general purpose CPU, a DSP, or an Application Specific Integrated Circuit that executes a calibration program stored in the memory system 108. The calibration program may follow the flow diagram steps shown in FIG. 2.

The CPU 106 determines the multiresolution decomposition 122 using, for example, a Burt pyramid decomposition of the image data 120 or another multiresolution decomposition technique. An example of a multiresolution decomposition technique is detailed in "Multiresolution Image Processing and Analysis", Ed. A. Rosenfield, Springer Series in Information Sciences, Springer Verlag, pp. 10–14 (1984). The resulting multiresolution decomposition 122 comprises numerous spatial frequency bands that represent image content across a series of resolution levels.

A multiresolution decomposition is a series of images, each of which is a low pass filtered copy of its predecessor. The original image may form the first of the series of images, and each subsequent image, because it is a low pass filtered copy of its predecessor, includes spatial frequency information at progressively smaller bands of frequencies. In other words, there is decreasing frequency content in each image in the series of images.

The digital image detector 109 may be characterized by its resolution. Typically, resolution is given in terms of a Modulation Transfer Function (MTF) that quantifies amplitude response of the digital image detector 109 to different spatial frequencies (e.g., a number of line pairs per millimeter). As the spatial frequency increases, the MTF of the digital image detector 109 decreases due to its finite resolution. In other words, the digital image detector 109 is only able to distinguish the lines and spaces of spatial frequencies up to a certain point (e.g., several line pairs/mm), after which the digital image detector 109 cannot distinguish lines from spaces.

As an aid to determining the MTF of the digital image detector 109, the digital imaging system 100 may employ an imaging phantom. An imaging phantom is a piece of material that carries a known calibration pattern, such as a series of lead bars separated by spaces. The thickness and spacing determine the spatial frequencies to be measured. The lead has large attenuation, the spaces little attenuation. The spatial variation of these step responses are used to determine the MTF as described below.

In particular, the bar pattern phantom 126 is one example of many types of phantoms that may be used to determine an MTF indicative of the resolution of a digital image detector. The bar pattern phantom 126 provides a series of lead strip spaced apart, preferably by 0.5 to 2.5 line pairs/mm (generally matched to the feature size to be detected using the digital image detector). The MTF, for each spatial frequency band, is determined according to how well the pixels in the band capture a step response generated by the lead strips on the bar pattern phantom 126. The MTF may be determined, for example, at twelve spatial frequencies corresponding to the following line pair groups: 0.50, 0.55, 0.60, 0.70, 0.80, 0.90, 1.0, 1.1, 1.2, 1.4, 1.6, 1.8 lp/mm according to:

$$MTF=(Pi*sqrt(2))/((4*Mean\ 0)*sqrt(VarFreq))$$

where:
VarFreq=|VarROI−VarNoise|
VarROI=Variance in the ROI
VarNoise=(VarBlack+VarWhite)/2
Mean 0=(MeanWhite−MeanBlack)/2

Each region of interest (ROI) may be defined, for example, to be in the center of each resolution group noted above. The size of each ROI is preferably set such that the ROI covers n−2 line pairs, where n is the total number of line pairs in the current group. For example, for groups with a total of five line pairs, the ROI covers three line pairs. Note that the above formula for MTF takes into consideration the mean and variance of the White and Black levels in the ROI as well as the noise of the background using the term VarNoise.

Other types of phantoms are also suitable for determining MTF, however. As an example, a phantom having a sharply defined edge (e.g., a tungsten or copper edge phantom) provides an edge image on the detector. The edge image transitions from black to white through a grey area. The Fourier Transform of the derivative of the edge response (line spread function) may then be used to calculate the MTF.

Absolute MTF is the MTF determined at a preselected region on the digital image detector, such as in the center. The spatial variation in MTF resolution uniformity may then be normalized to the absolute MTF as described below.

The resolution uniformity may be measured by imaging a mesh pattern (e.g., the uniformity mesh 128 which is preferably a stainless steel mesh having a spatial frequency that depends on the detector limiting resolution). In one embodiment, the uniformity mesh 128 has a frequency of approximately 1.5 line pairs/mm (e.g., approximately ⅗ of the limiting resolution of 2.5 lines pairs/mm). The ratio of the standard deviation to the mean image level in regions of interest around the digital image detector give a relative estimate of the local resolution in that region across all spatial frequency bands. The resolution uniformity may be normalized with respect to the ratio measurement at the center of the image.

The flat phantom 124 may be used to determine Noise Power Spectrum (NPS) of the digital image detector 110. The flat phantom 124 has a uniform thickness. By subtracting two flat field images, the resultant difference image characterizes digital image detector NPS. As an example, the radial average of the Fourier transform of the difference image provides a measure of NPS.

Weighting coefficients, Coef(i), determine within a given band "i", the amount of MTF adjustment (which may result in an increase or a decrease in MTF). Generally stated, for each frequency band, "i", over the range of frequency bands:

$$Coef(i) = \text{Function}(\text{Desired\_Performance}(i), \text{Raw\_Performance}(i))$$

and, as one example, $$Coef(i) = \text{Desired\_Performance}(i)/\text{Raw\_Performance}(i)$$

such that if Desired_Performance(i)=100 (e.g., perfect reproduction of the bar pattern phantom 126 step response) and Raw_Performance(i)=50, then Coef(i)=2. Desired_Performance(i) is preferably the predetermined desired resolution (e.g., a target MTF) at the spatial frequency band "i", and Raw_Performance(i) is preferably the measured (e.g., the unadjusted initial) resolution at the spatial frequency band "i".

Coef(i) may then be applied to each pixel value p(x, y, i) in each spatial frequency band to form new pixel values p'(x, y, i)=Coef(i) * p(x, y, i). Other linear and non linear functions may also be used, however.

Rather than applying a single weighting coefficient to every pixel in a particular spatial frequency band, the resolution calibration subsystem 102 may determine multiple weighting coefficients to provide a weighting coefficient for each of several regions of pixels, or for every pixel in a spatial frequency band. Thus, Coef(i) may be replaced by Coef(x, y, i) based on a measurement of resolution uniformity (e.g., MTFU): p'(x, y, i)=Coef(x, y, i) * p(x, y, i).

In some instances, the resolution uniformity follows a particular pattern on the digital image detector, such as a radial pattern. The resolution calibration subsystem 102 may use this pattern to more quickly determine (by taking fewer measurements) and apply Coef(x, y, i) to the pixels in the spatial frequency bands. The term R(x, y) is used below to indicate the normalized spatially dependent resolution factor relative to the center of the digital image detector (where absolute MTF is determined). In general, Coef(x, y, i) =Coef(i) * R(x, y).

Although the resolution may be enhanced by multiplying pixel values by the weighting :coefficients, too much enhancement may undesirably impact noise content in the image. In general, since the output signal to noise ratio (SNR) (a function of frequency, f) remains unchanged when the resolution is enhanced:

$$SNR(f) = C^*[MTF_A(f)]^2/[NPS_A(f)] = C^*[MTF_B(f)]^2/[NPS_B(f)] = C^*[alpha(f)^*MTF_A(f)]^2/[alpha(f)^2 * NPS_A(f)]$$

where C is a factor that depends on exposure, X-ray beam quality, and the like, alpha is the amount of MTF enhancement applied (e.g., the magnitude of the weighting coefficient in the discrete case), A is the raw (measured image value) and B is the compensated (processed) image value. As can be seen, resolution enhancement linearly affects MTF, but affects noise according to the square of alpha(f). Rapid increases in MTF therefore result in far more rapid increases in noise. In order to prevent the introduction of too much noise into an image, the resolution calibration subsystem 102 may cap the weighting coefficients according to a noise factor, for each resolution band and for each pixel, according to:

$$Coef(x, y, i) = \min(Coef(x, y, i), \text{Noise\_Factor}),$$

as one example, $$Coef(x, y, i) = \min((MTF_D(i)/MTF_R(i))^*R(x, y), sqrt(NPS_M(i)/NPS_R(i)))$$

where sqrt is the square root function, subscript D indicates a desired value, subscript R represents a raw (measured value), and subscript M indicates a preselected maximum (i.e., $NPS_M(i)$ is the preselected maximum noise allowable according to customer CTQ specification, for example).

After the weighing coefficients have been applied in each spatial frequency band, the medical imaging system 100 may apply any additional image processing (such as contrast enhancement), then reconstruct an image for display.

The calibration of image resolution is not limited to the discrete (pixel image) case. Rather, the calibration of image detector resolution may be extended to the continuous time case, as described in more detail below.

In a continuous time system (in which discrete values of Coef(i) are replaced by a continuous calibration factor alpha(f)):

$$alpha(f) = \min(\text{Noise\_Factor}(f), MTF_D(f)/MTF_R(f))$$

as one example, $$alpha(f) = \min(sqrt(\text{beta}(f)), MTF_D(f)/MTF_R(f)),$$

where $$NPS_R(f) = (1/\text{beta}(f)) * NPS_M(f),$$

and, typically, $$MTF_D(f) >= MTF_R(f) \text{ and beta}(f) >= 1.0$$

In the general case, a digital filter may be designed with the frequency response characterized by alpha(f). A continuous image signal may then be applied to the filter to achieve the desired resolution calibration. Referring again to FIG. 1, an image input signal 150 may thus be applied to a resolution calibration filter 152. The resolution calibration filter 152 produces, as a result, a resolution calibrated signal output 154.

In a multiresolution decomposition, such as that described above, the calibration factor alpha(f) is replaced by a discrete coefficient, Coef(i) (e.g., over i=0 to 7 resolution levels in the multiresolution decomposition):

$$Coef(i) = \frac{1}{(f2 - f1)} \int_{f1}^{f2} alpha(f) df \text{ and}$$

$$f1 = \frac{N}{2^{(i+1)}}, \quad f2 = \frac{N}{2^i}$$

where N=the Nyquist frequency of the digital image detector (e.g., 2.5 line pairs/mm). Coef(i) is thus, preferably, the average of the calibration factor alpha(f) over the given range.

Figure 2:
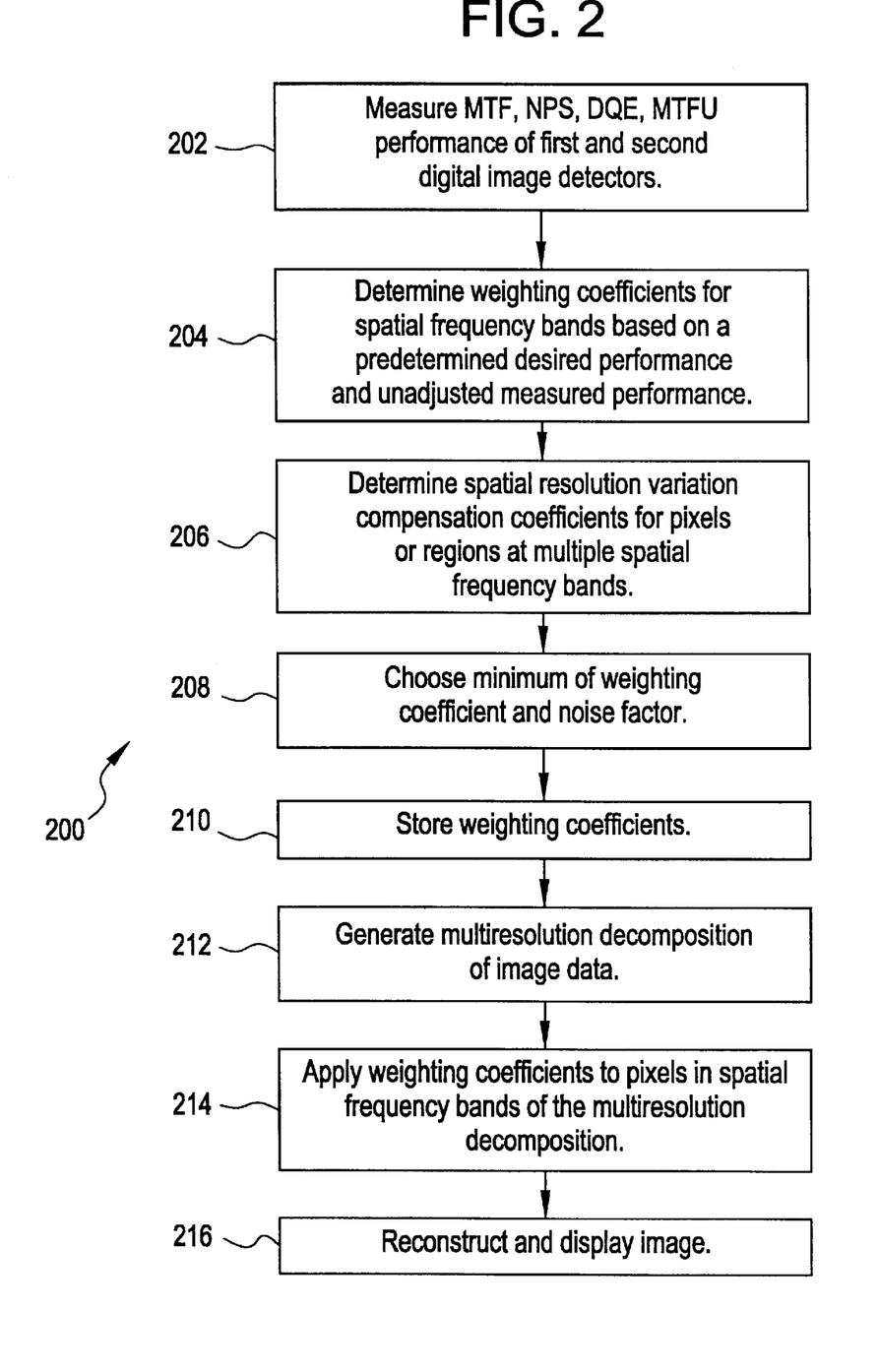
FIG. 2 shows a flow diagram for calibrating the resolution of a digital medical imaging system.

Turning now to FIG. 2, that figure illustrates a flow diagram 200 for calibrating the resolution of a digital medical imaging system. At step 202, a resolution adjustment system (e.g., the medical imaging system 100, or a factory calibration system) measures unadjusted performance of a digital image detector. The unadjusted performance may correspond to a MTF, MTFU, NPS, or SNR, as examples. Because it may be desirable to match two or more associated digital imaging systems that will be installed at a single location, for example, the resolution adjustment system may measure unadjusted performance on two or more digital image detectors to be used in the associated digital imaging systems.

Next, at step 204, the resolution adjustment system determines weighting coefficients for spatial frequency bands processed by a medical imaging system. The weighting coefficients are preferably based on a desired performance (as specified by customer CTQ numbers, for example) and the measured unadjusted performance of the digital image detector. Furthermore, when matching two systems, the weighting coefficients for the digital image detector in the second system may be based on a preselected desired performance of the first digital image detector and the measured unadjusted. performance of the second digital image detector. In other words, weighting coefficients are chosen such that both systems achieve the same preselected desired adjusted resolution. Note that matching digital imaging systems to a preselected resolution may, in fact, require a decrease in a system's resolution or MTF if the particular digital image detector in that system is exceptional. Furthermore, the process of matching systems may proceed based on any particular reference. Thus, an overall resolution standard may be set by the digital imaging system manufacturer. Then, the digital imaging systems produced by that manufacturer may all be matched to the resolution standard.

At step 206, the resolution adjustment system determines, optionally, spatial resolution variation compensation weighting coefficients for individual pixels at each spatial resolution level. As described above, the spatial resolution variation compensation weighting coefficients, Coef(x, y, i), compensate for changes in resolution uniformity over the digital image detector 110. A weighting coefficient may be determined for each pixel in each spatial resolution level, or a smaller set of weighting coefficients may be determined for use among pixels in larger regions of each spatial resolution level. Alternatively, the weighting coefficients may be set to a constant, Coef(x, y, i)=Coef(i), indicating no correction for resolution uniformity.

At step 208, the resolution adjustment system preferably ensures that the weighting coefficients are not so large that their application would exceed a maximum desired noise factor in the resulting processed image. In other words, the resolution adjustment system may replace any weighting coefficient with the minimum of the weighting coefficient and a noise factor, as described above. At step 210, the resolution adjustment system stores the coefficients for the digital detector in a memory for future use by the medical imaging system incorporating the digital detector.

Before the medical imaging system 100 displays an image, the CPU 106 preferably; generates a multiresolution decomposition 122 of the image data 120 (step 212). As noted above, the multiresolution decomposition 122 includes numerous resolution levels corresponding to spatial frequency bands in the image. The CPU 106 applies, at step 214, the weighting coefficients determined for each pixel, region, or spatial frequency band. Next, at step 216, the CPU 106 reconstructs an image for display using the resolution enhanced multiresolution representation of the image.

Figure 3:
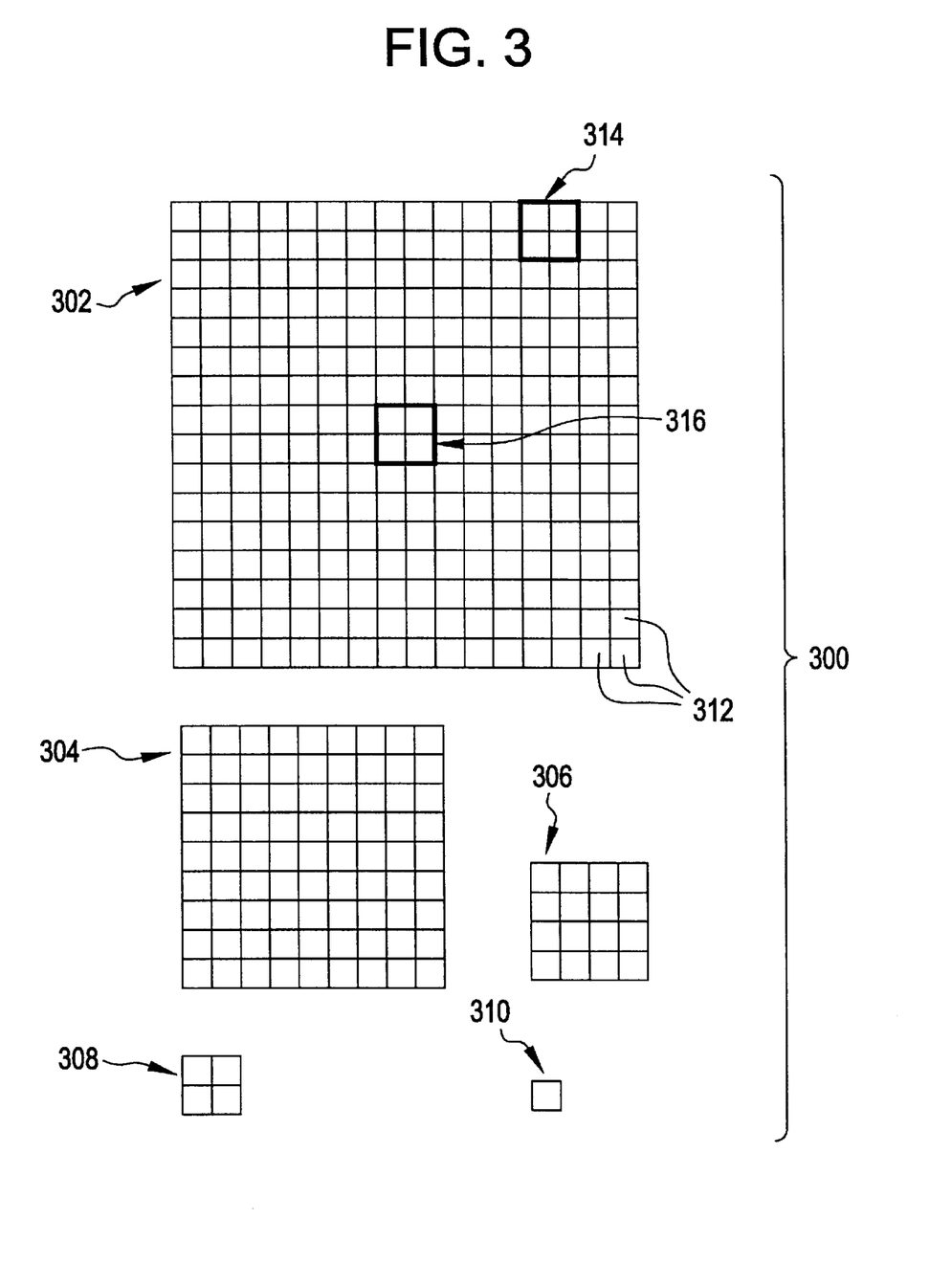
FIG. 3 depicts a multiresolution image decomposition, including a digital image at a particular spatial frequency band.

Turning next to FIG. 3, that figure illustrates a multiresolution image decomposition 300. The decomposition 300 shows resolution levels 302–310 (additional or fewer may be used in practice) associated with particular spatial frequencies in the decomposition 300. Each resolution level 302–310, for example, the resolution level 302, is comprised of pixels 312. The pixels 312 may be grouped into regions of a preselected shape and number of pixels. An outlying region 314 and a central region 316 are indicated in FIG. 3.

The central region 316 specifically covers the center of the digital image detector and represents the area in which the absolute MTF is preferably determined (as noted above). Spatial variation in image resolution is measured outside of the central region 316, for example, in one or more outlying regions (e.g., the outlying region 314). As noted above, a single weighting coefficient may be determined for an entire spatial frequency band 302–310, multiple weighting coefficients may be determined to provide a weighting coefficient for each region 314, 316 in each spatial frequency band 302–310, or multiple weighting coefficients may be determined to provide a weighting coefficient for each pixel 312 in each spatial frequency band 302–310. The multiple weighting coefficients are preferably spatial resolution variation compensation weighting coefficients Coef(x, y, i) determined as indicated above. The weighting coefficients are applied (e.g., multiplied with) the pixel values in each spatial frequency band 302–310 or region 314, 316 before image reconstruction to compensate the digital image detector to the desired resolution.

Figure 4:
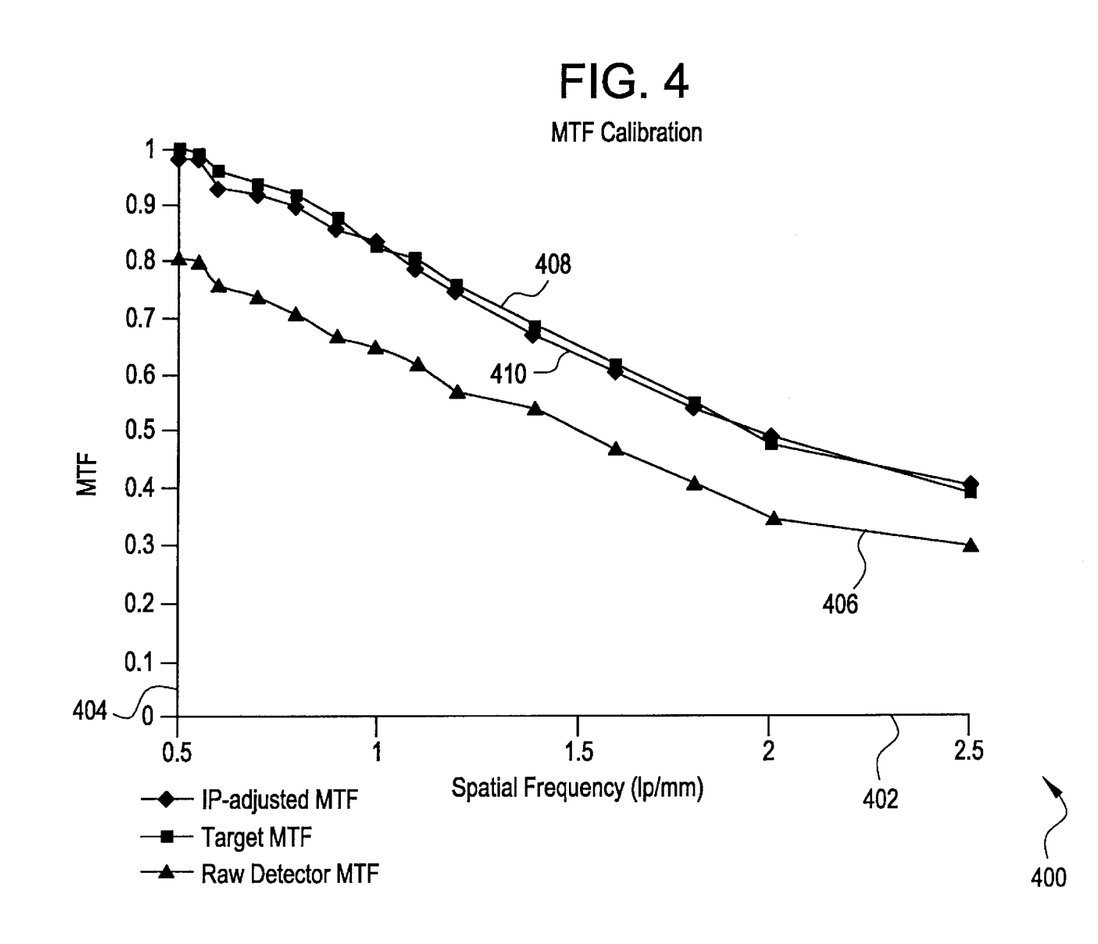
FIG. 4 shows one example result of resolution adjustment of a digital image detector.

Turning to FIG. 4, a graph 400 shows one example result of resolution adjustment. The graph has a spatial frequency axis 402 and an MTF axis 404. A raw (measured) MTF line 406, a target MTF line 408, and an achieved MTF line 410 are present in FIG. 4. Using the resolution adjustment techniques described above, the raw MTF improves to the level shown by the achieved MTF line 410. The achieved MTF line 410 further shows close correspondence to the preselected desired or target MTF line 408, over the frequencies of interest.

The present invention thereby provides the ability to relax resolution specifications of a digital image detector (through image processing resolution enhancement). Yield is correspondingly increased. The present invention also allows calibration to a specific system level resolution according to a customer CTQ specification while limiting the amount of resolution enhancement to achieve noise-related performance goals. The present invention may also be used as part of a fully automatic digital imaging system calibration, and to achieve resolution consistency among numerous digital image detectors and digital imaging systems. Furthermore, the method and apparatus described allow spatial adjustment of the resolution coefficients to achieve uniform resolution over the entire digital image detector.

What is claimed is:

1. A resolution calibration subsystem for a medical imaging system employing a digital image detector, the resolution calibration subsystem comprising:

a memory storing digital image data;

a processor coupled to the memory, the processor determining a first spatial frequency band of the image data and applying a weighting coefficient to the first spatial frequency band, wherein the processor calculates the weighting coefficient based on a predetermined desired resolution of a digital image detector and a measured resolution of the digital image detector.

2. A resolution calibration subsystem according to claim 1, wherein the processor determines an additional spatial frequency band of the image data and applies an additional weighting coefficient to the additional spatial frequency band, wherein the additional weighting coefficient is based on the desired resolution of the digital image detector and the measured resolution of the digital image detector.

3. A resolution calibration subsystem according to claim 1, wherein the processor calculates a plurality of weighting coefficients that are spatial resolution variation compensation coefficients.

4. A resolution calibration subsystem according to claim 3, wherein spatial resolution variation compensation coefficients include a spatially dependent resolution factor relative to a center of an image represented by the image data.

5. A resolution calibration subsystem according to claim 3, wherein the processor applies the weighting coefficients by multiplying the weighting coefficient for each region against pixel values of the region.

6. A resolution calibration subsystem according to claim 1, wherein the weighting coefficient is a function of a desired Modulation Transfer Function of the digital image detector and a measured Modulation Transfer Function of the digital image detector.

7. A resolution calibration subsystem according to claim 1, wherein the weighting coefficient is a minimum of the weighting coefficient and a noise factor.

8. A resolution calibration subsystem according to claim 1, wherein the processor applies the weighting coefficient by multiplying the weighting coefficient against pixel values of the spatial frequency band.

9. A medical imaging system providing resolution control over a digital image detector, the medical imaging system comprising:
   a resolution measuring unit that obtains at least one resolution characteristic of a digital image detector that collects image data; and
   a processor calculating at least one weighting coefficient based on a predetermined desired resolution of the digital image detector and at least one resolution characteristic of the digital image detector, in order to provide resolution control.

10. A resolution calibration subsystem according to claim 9, wherein the processor determines multiple spatial frequency bands of the image data and applies multiple different weighting coefficients to the multiple spatial frequency bands, wherein the multiple weighting coefficients are based on the desired resolution of the digital image detector and a measured resolution of the digital image detector.

11. A resolution calibration subsystem according to claim 9, wherein the processor calculates a plurality of weighting coefficients that are spatial resolution variation compensation coefficients.

12. A resolution calibration subsystem according to claim 11, wherein spatial resolution variation compensation coefficients include a spatially dependent resolution factor relative to a center of an image represented by the image data.

13. A resolution calibration subsystem according to claim 11, wherein the processor applies the weighting coefficients by multiplying the weighting coefficient for each region of image data against pixel values of the region.

14. A resolution calibration subsystem according to claim 9, wherein the weighting coefficient is a function of a desired Modulation Transfer Function of the digital image detector and a measured Modulation Transfer Function of the digital image detector.

15. A resolution calibration subsystem according to claim 9, wherein the processor applies the weighting coefficient to the image data by multiplying the weighting coefficient against pixel values of a spatial frequency band of the image data.

16. A method for calibrating resolution of a digital imaging system, the method comprising:
   obtaining an initial resolution characteristic of a digital image detector to be used in a medical imaging system;
   obtaining a resolution weighting coefficient for medical imaging system based on a target resolution characteristic of the first digital image detector and the initial resolution characteristic of the digital image detector; and
   using the resolution weighting coefficient to calibrate resolution of the medical imaging system.

17. A method according to claim 16, wherein the step of obtaining a weighting coefficient comprises determining a plurality of weighting coefficients for a first spatial frequency band.

18. A method according to claim 16, wherein the step of obtaining comprises determining multiple weighting coefficients to compensate for spatial variations in an unadjusted performance of the digital image detector.

19. A method according to claim 16, wherein the obtaining step comprises measuring at least one of a Modulation Transfer Function, Modulation Transfer Function uniformity, Noise Power Spectrum, and Signal to Noise Ratio.

20. A method for calibrating resolution of a digital imaging system, the method comprising:
   measuring unadjusted performance of a first digital image detector to be used in a medical imaging system;
   determining a weighting coefficient for a first spatial frequency band processed by the medical imaging system based on a desired performance of the first digital image detector and the measured unadjusted performance of the first digital image detector, wherein the weighting coefficient is set equal to a minimum of the weighting coefficient and a noise factor; and
   storing the weighting coefficient for subsequent application to the spatial frequency band by the medical imaging system.

21. A resolution calibration subsystem for a medical imaging system employing a digital image detector, the resolution calibration subsystem comprising:
   a memory storing digital image data; and
   a processor coupled to the memory, the processor calculating a plurality of weighting coefficients based on a predetermined desired resolution of a digital image detector and a measured resolution of the digital image detector, the processor determining a first spatial frequency band of the image data and applying the plurality of weighting coefficients to individual regions of the first spatial frequency band.

22. A medical imaging system providing resolution control over a digital image detector, the medical imaging system comprising:
   a resolution measuring unit that obtains at least one resolution characteristic of a digital image detector that collects image data; and
   a processor calculating a plurality of weighting coefficients based on a predetermined desired resolution of the digital image detector and at least one resolution characteristic of the digital image detector, the processor applying the plurality of weighting coefficients to individual regions of a first spatial frequency band in order to provide resolution control.

23. A medical imaging system providing resolution control over a digital image detector, the medical imaging system comprising:

a resolution measuring unit that obtains at least one resolution characteristic of a digital image detector that collects image data; and a processor calculating at least one weighting coefficient based on a predetermined desired resolution of the digital image detector and at least one resolution characteristic of the digital image detector in order to provide resolution control, wherein the weighting coefficient is a minimum of the weighting coefficient and a noise factor.

* * * * *